| United States Patent [19] | [11] 4,035,367 |
|---|---|
| Simpson | [45] July 12, 1977 |

[54] HYDROXYALKYL-SUBSTITUTED-AMINO-QUINOLINES

[75] Inventor: William R. Simpson, Mendham, N.J.

[73] Assignee: Sandoz, Inc., E. Hanover, N.J.

[21] Appl. No.: 656,246

[22] Filed: Feb. 9, 1976

Related U.S. Application Data

[60] Division of Ser. No. 504,427, Sept. 9, 1974, Pat. No. 3,957,791, which is a division of Ser. No. 291,833, Sept. 25, 1972, Pat. No. 3,856,796, which is a continuation-in-part of Ser. No. 245,308, April 19, 1972, abandoned, which is a continuation-in-part of Ser. No. 127,376, March 23, 1971, abandoned.

[51] Int. Cl.$^2$ .............. C07D 295/08; C07D 215/42
[52] U.S. Cl. .................... 260/268 BQ; 260/286 R; 260/288 R
[58] Field of Search ..... 260/268 BQ, 286 R, 288 R

[56] References Cited

U.S. PATENT DOCUMENTS

| 3,173,918 | 3/1965 | Baget et al. ................. 260/268 BQ |
| 3,272,824 | 9/1966 | Ebetino et al. .............. 260/268 BQ |
| 3,702,849 | 11/1972 | Cronin et al. ............... 260/268 BQ |

FOREIGN PATENT DOCUMENTS

| 7,357M | 10/1969 | France |
| 1,620,489 | 4/1970 | Germany |

*Primary Examiner*—Paul M. Coughlan, Jr.
*Attorney, Agent, or Firm*—Gerald D. Sharkin; Richard E. Vila

[57] ABSTRACT

Disclosed are compounds of the class of quinolines substituted at the 2-, 3- or 4-position by an amino function bearing a hydroxyalkyl nitrate moiety, e.g. 4-(2-hydroxyethylpiperazino)-quinoline nitrate. The compounds have various pharmacological activities in animals and are useful, for example, as hypotensive and anti-anginal agents. Also disclosed are the corresponding hydroxy intermediates which are useful in preparation of the nitrates and also as hypotensive and anti-anginal agents.

12 Claims, No Drawings

HYDROXYALKYL-SUBSTITUTED-AMINO-QUINOLINES

This application is a division of application Ser. No. 504,427, filed Sept. 9, 1974, now U.S. Pat. No. 3,957,791, which is a division of application Ser. No. 291,833, filed Sept. 25, 1972, now U.S. Pat. No. 3,856,796, which in turn is a continuation-in-part of application Ser. No. 245,308, filed Apr. 19, 1972 which in turn is a continuation-in-part of application Ser. No. 127,376, filed Mar. 23, 1971, now both abandoned.

This invention relates to quinoline derivatives, and more particularly to pharmacologically active quinolines which are substituted at the 2-, 3- or 4- position by an amino function bearing a hydroxyalkyl nitrate moiety. The invention further relates to corresponding hydroxyalkyl substituted amino-quinolines useful as intermediates in preparation of said nitrates and also possessing pharmacological activity. The invention also relates to pharmaceutical methods and compositions utilizing said compounds.

The compounds of the invention may be represented by the structural formula I:

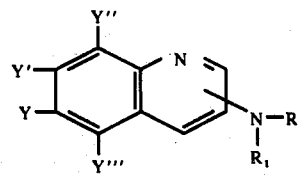

wherein
R is from the group of
  a. $-CH_2(-CH_2)_n-ONO_2$ b) $-CH_2(-\overset{R^\circ}{\underset{|}{CH}})_n-ONO_2$, and c) $-\overset{R'}{\underset{|}{CH}}(-CH_2)_n-ONO_2$ d. $-CH_2(-CH_2)_z-N[-CH_2(-CH_2)_y-ONO_2]_2$ $R_1$ is from the group of
  e. $-CH_2(-CH_2)_n-ONO_2$ when R is a) as above defined,
  f. hydrogen, and
  g. lower alkyl of 1 to 4 carbon atoms, R' is $-(CH_2-)_xCH_3$ or $-(CH_2)_yONO_2$,
R° is hydrogen, $-(CH_2-)_mCH_3$ or $-(CH_2-)_yONO_2$, provided that one R° (and only one) is other than hydrogen, that the sum of $n$ and $m$ does not exceed 7 and that the sum of $n$ and $y$ does not exceed 8, or R and $R_1$ together with the 4- amino nitrogen attached to the quinoline ring form

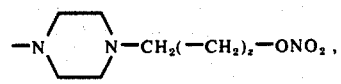

$n$ is 1 to 7, preferably 3 to 5,
$m$ is 0 to 4,
$x$ is 0 or 1,
$y$ is 1 to 4,
$z$ is 1 to 4, and each of Y, Y', Y'' and Y''' is hydrogen, halo of atomic weight of from 18 to 80, i.e., fluoro, chloro or bromo, lower alkoxy of 1 to 3 carbon atoms, e.g., methoxy or lower alkyl of 1 to 3 carbon atoms, e.g., methyl, or Y and Y' together form methylenedioxy; provided that at least 2 of Y, Y', Y'' and Y''' are hydrogen and further provided that when one of Y, Y', Y'' and Y''' is halo then the others are hydrogen, or a 1-lower alkyl($C_1$-$C_3$-)iodide, the 1-trifluoromethyl iodide or the 1-($\omega,\omega,\omega$-trifluoro)ethyl iodide thereof.

A preferred method for preparation of the compounds of formula I involves in a Step A reaction the nitration of the corresponding hydroxy compound of formula II:

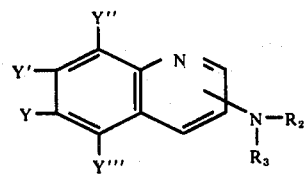

or a corresponding iodide thereof, wherein $R_2$ and $R_3$ are the non-nitrate bearing hydroxyalkyl substituents corresponding to R and $R_1$, respectively, i.e.:
$R_2$ is from the group of:
  a. $-CH_2(-CH_2)_n-OH$ b) $-CH_2(-\overset{R^\circ_a}{\underset{|}{CH}})_n-OH$, and c) $-\overset{R'_a}{\underset{|}{CH}}(-CH_2)_n-OH$ d. $-CH_2(-CH_2)_z-N[-CH_2(-CH_2)_y-OH]_2$ $R_3$ is from the group of:
  e. $-CH_2(-CH_2)_n-OH$ when $R_2$ is a) as above defined,
  f. hydrogen,
  g. lower alkyl of 1 to 4 carbon atoms,
$R_a'$ is $-(CH_2)_xCH_3$ or $-(CH_2)_yOH$, $R_a^\circ$ is hydrogen, $-(CH_2-)_mCH_3$ or $-(CH_2-)_yOH$, provided that one $R_a^\circ$ is other than hydrogen, that the sum of $n$ and $m$ does not exceed 7 and that the sum of $n$ and $y$ does not exceed 8, or
$R_2$ and $R_3$ together with the 4- amino nitrogen attached to the quinoline ring form

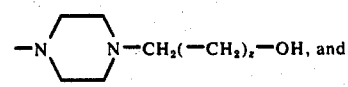

$n$, $m$, $y$ and $z$ and Y, Y', Y'' and Y''' are as defined.

The preparation of compounds I by step A involves a nitration reaction which may be carried out in a manner known per se for nitrating hydroxyalkyl groups. A preferred method of conducting the nitration involves the reaction of a compound II with nitric acid in presence of a carboxylic acid anhydride which is preferably of from 3 to 8 carbon atoms, more preferably acetic acid anhydride. The reaction may be suitably carried out in an organic solvent medium at temperatures in the range of from minus 70° to plus 50° C., preferably minus 5° to plus 20° C. The solvent medium for the reaction is preferably provided by employing a lower aliphatic carboxylic acid, e.g., acetic acid, although other well known organic solvents may be employed or the reaction may be carried out employing an excess of the carboxylic acid anhydride. The product compound I may be isolated from the reaction mixture of Step A by working up by established procedures.

A preferred method for preparation of compounds II involves a step B reaction of a corresponding haloquinazoline of formula III:

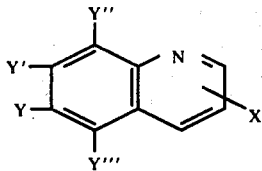

or a corresponding iodide thereof, wherein Y, Y', Y'' and Y''' are as defined and X is halo from the group of chloro or bromo, preferably chloro with a compound of formula IV:

wherein $R_2$ and $R_3$ are as defined.

The reaction of Step B is of known type and may be carried out in a conventional manner by subjecting a compound III to reaction with the compound IV at elevated temperatures which may be suitably in the range of 30° to 180° C., preferbly 60° to 160° C. The reaction may be suitably carried out in an inert organic solvent which may be any of several of the well-known conventional solvents such as dioxane. A generally preferred solvent is isopropanol. Alternately, the reaction may be initiated and/or carried out in the inert liquid medium provided by employing an excess of compound IV when the compound is liquid at the reaction temperature or by fusion of solid reactants. An acid binding agent such as sodium carbonate may be also employed to advantage in the reaction, if desired. The reaction product compound II may be isolated from the reaction mixture of Step B by established procedures.

However, the preferred procedures for the preparation of the iodides of the compounds of the formulae I and II involves reacting the corresponding compound of the formulae I and II, respectively, with the iodides at temperatures in the range of from 20° to 100° C. The reaction may be carried out in inert organic solvents of conventional type but it is generally preferred to use an excess of the iodide as the sole solvent and conduct the reaction at the reflux temperature of the system.

The compounds of formula III and IV are either known or may be prepared from known materials by established procedures.

The compounds of the formulae I and II may be produced in the form of acid addition salts and the pharmaceutically acceptable acid addition salts are also included within the scope of the invention. Such salts include the acid addition salts, e.g., the methane sulfonate, hydronitrate, hydrosulfonate, fumarate, hydrochloride and maleate. Such salts may then be readily converted to the free bases by conventional procedures. In preparing the free bases from the acid addition salt, it is also convenient to employ a buffer system, e.g., a system comprising a 1:1 molar mixture of acetic acid and sodium acetate, followed by working up by conventional procedures. The free bases may be readily converted into the hydronitrate and other acid addition salts by established procedures.

The compounds of the formula I and II (including their iodides) and their pharmaceutically acceptable acid addition salts, are useful because they possess pharmacological activity in animals. In particular, the compounds of the formulae I and II are useful as agents for the lowering of blood pressure, e.g., as hypotensive agents, as indicated on intravenous administration to the anesthetized dog in the Cannulated Blood Vessel Test. The compounds of formulae I and II are also useful as antianginal agents as indicated by effecting coronary dilation in the anesthetized dog on intravenous administration and measurement of blood flow through the anterior descending branch of the left coronary artery.

The compounds of formulae I and II (including their iodides) are further useful as anti-arrhythmic agents, as indicated by polygraph recordings on intravenous administration to the anesthetized dog given Oubain until the appearance of constantly occurring ventricular ectopic beats and then the test compound every two minutes until the arrhythmia reverts to sinus rhythm.

For the above uses, the compounds of the formulae I and II may be combined with a pharmaceutically acceptable carrier, and such other conventional adjuvants as may be necessary, and administered orally in such forms as tablets, capsules, elixirs, suspensions and the like or parenterally in the form of an injectable solution or suspension. For the above-mentioned uses, the dosage administered will, of course, vary depending upon the compounds used, the therapy desired and the mode of administration. However, for use as agents for the lowering of blood pressure, e.g. as hypotensive agents, and for use as anti-arrhythmic agents, satisfactory results in general are obtained with the compounds of the formula I and II when administered at a daily dosage of from about 0.2 milligrams to about 100 milligrams per kilogram of body weight, preferably given in divided doses 2 to 4 times a day, or in sustained release form. For most larger mammals, the administration of from about 16 milligrams to about 500 milligrams of the compond per day provides satisfactory results and dosage forms suitable for internal administration comprise from about 4 milligrams to about 250 milligrams of the compound in admixture with a solid or liquid pharmaceutical carrier or diluent.

As anti-anginal agents, satisfactory results may be obtained with the compounds of the formulae I and II when administered at a daily dosage of from 0.2 to 100 milligrams per kilogram of body weight, given as required or in divided doses or in sustained release form. For most larger mammals, a dosage of from 16 to 500 milligrams, pro re nata, provides satisfactory results. As anti-anginal agents, the compounds are preferably administered orally and used to prophylactically prevent or minimize angina attacks at a daily dosage of 16 to 500 milligrams, or in divided doses of from 4 to 240 milligrams. The preferred anti-anginal compounds are those of the formula I.

Various of the compounds of the invention as represented by the compounds of Examples 4z-1), 4z-9) and 3a) hereinafter also possess peripheral vasodilatory activity as indicated in dogs by the cannulated blood vessel test following intravenous administration, and are therefore also indicated for use as peripheral vasodilators. The indicated suitable modes of administration and daily dosage are the same as for the indicated hypotensive use, above.

The compounds of formula II (including their iodides) are also useful as anti-obesity agents as indicated by glucose transport tests carried out on male Wistar rats which are dosed orally with 10–150 milligrams per kilogram of body weight of the test compound after at least 20 hours of fasting. One hour after receiving the drug each animal is sacrificed and the upper small intestine is removed and washed with glucose-saline. A 5 cm. section of the intestine is everted so that the mucosal surface is on the outside. One end of the segment is tied off and the center of the sac so formed is filled with oxygen saturated Kreb's bicarbonate buffer. The other end is then closed and the sac is incubated in 10 ml. of oxygen saturated bicarbonate buffer for 60 minutes at 37° C. Both the outside and inside solutions contain initially 0.3% of glucose. At the end of the incubation time, the glucose content of the outer (mucosal) and the inner (serosal) solution is determined using the standard Autoanalyzer procedure. Similar tests are run simultaneously with control animals. The percent inhibition of glucose transport caused by the drug is calculated from the formula:

$$I = \frac{S_t - M_t}{S_c - M_c} \times 100$$

where
I = percent inhibition;
$S_t$ = glucose concentration (mg.%) of serosal fluid at the end of an experiment in the drug-treated animal;
$S_c$ = glucose concentration (mg.%) of serosal fluid at the end of an experiment in the control animal;
$M_t$ = glucose concentration (mg.%) of mucosal fluid at the end of an experiment in the drug-treated animal; and
$M_c$ = glucose concentration (mg.%) of mucosal fluid at the end of an experiment in the control animal.

The effective dosage of active ingredient employed for the treatment of obesity will vary depending on the particular compound employed and the severity of the condition being treated. However, in general, satisfactory results in the treatment of obesity are obtained when the compounds II are administered at a daily dosage of from about 0.3 milligrams to about 150 milligrams per kilogram of animal body weight, preferably given in divided doses two to four times a day, or in sustained release form. For most large mammals, the total daily dosage is from about 30 to 1000 milligrams. Dosage forms suitable for internal use comprise from about 10 to about 500 milligrams of the active compound in intimate admixture with a solid or liquid pharmaceutically acceptable carrier or diluent.

The preferred anti-obesity agents of the formula II are those in which $R_2$ is a), b), c) and d) as defined above with respect to compounds II, more preferably in other than iodide form with $R_3$ being hydrogen and with the $-NR_2R_3$ moiety being at the 4-position. More particularly preferred as anti-obesity agents among $R_2$ being a), b), c) and d) are those in which $R_2$ is d), usually with $R_3$ being hydrogen and in other than iodide form, for example, the compound of Example 4(s) hereinafter.

For the above usages, oral administration with carriers may take place in such conventional forms as tablets, dispersible powders, granules, capsules, syrups and elixirs. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, i.e., inert diluents such as calcium phosphate, calcium sulphate dihydrate, lactose and talc, granulating and disintegrating agents, e.g., starch and alginic acid, binding agents, e.g., starch, gelatin, polyvinyl pyrrolidone and acacia, and lubricating agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan mono-oleate) and preservatives (ethyl-p-hydroxybenzoate). Capsules may contain the active ingredient alone or admixed with an inert solid diluent, e.g., calcium carbonate, calcium phosphate and kaolin.

A representative formulation is a tablet for administration orally two to four times a day to prevent or lessen the severity of angina attacks and prepared by conventional tabletting techniques to contain the following ingredients:

| Ingredients | Weight (mg.) |
| --- | --- |
| Compound of the formula I, e.g. 4-(5-hydroxypentyl)amino-7-methoxy-quinoline nitrate maleate | 50 |
| Tragacanth | 10 |
| Corn starch | 25 |
| Lactose | 197.5 |
| Talcum | 15 |
| Magnesium stearate | 2.5 |

A particularly preferred compound for the treatment of angina and/or arrhythmia is 1-methyl-4-(5-hydroxypentyl)amino-8-methoxyquinoline nitrate iodide and tablets containing 30 milligrams (instead of 50 milligrams) thereof may be formulated as given above for administration two to four times a day for use in such treatments.

In general, the compositions of the invention adapted for either oral or parenteral administration may contain 1% to 90% by weight of the active ingredient in combination with the inert carrier, more usually 3% to 40%.

The following examples are given for the purpose of illustration only.

EXAMPLE 1

2-[3-Bis(2-hydroxyethyl)aminopropyl]amino-quinoline dinitrate dihydrochloride

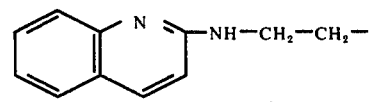

-continued

—CH₂—N(—CH₂—CH₂ONO₂)₂ . 2HCl

Step A: Preparation of 2-[3-bis(2-hydroxyethyl)aminopropyl]amino-quinoline.

A mixture of 5.05 g. of 2-chloroquinoline, 5.5 g. of bis(2-hydroxyethyl)aminopropylamine and 3.0 g. of sodium carbonate is heated in 20 ml. of refluxing isopropanol for 24 hours. The reaction mixture is then filtered, solvent removed in vacuo and the residue chromatographed over silica gel to obtain an oil of 2-[3-bis(2-hydroxyethyl)aminopropyl]amino-quinoline.

Step B: Preparation of 2-[3-bis(2-hydroxyethyl)aminopropyl]aminoquinoline dinitrate dihydrochloride.

A solution of 5.0 g. of 2-[3-bis(2-hydroxyethyl)aminopropyl]amino-quinoline in 5.0 g. of glacial acetic acid is added slowly to a stirred cooled (−5° C.) mixture of 15.0 ml. of acetic anhydride and 5.0 ml. of 90% nitric acid. Stirring is continued for 20 minutes after addition and 500 ml. of diethyl ether added to obtain an oil which is added to an excess of cooled (0° C.) aqueous ammonia solution. The resulting mixture is extracted with ethyl acetate, the organic phase dried and concentrated in vacuo to obtain an oil which is treated with a slight excess of hydrogen chloride in ethanol. Addition of diethyl ether yields a solid which is recrystallized from methanol/diethyl ether to obtain 2-[3-bis(2-hydroxyethyl)aminopropyl]amino-quinoline dinitrate dihydrochloride, m.p. 112° C. (decomp.)

EXAMPLE 3

Following the procedure of Example 1, the following compounds are pepared:

a. 2-[4-(2-hydroxyethyl)-1-piperazino]-quinoline.
b. 2-[4-(2-hydroxyethyl)-1-piperazino]-quinoline nitrate dihydrochloride, m.p. 263° C. (decomp.).
c. 2-(5-hydroxypentyl)amino-6,7-dimethoxy-quinoline, m.p. 127°–128° C.
d. 2-(5-hydroxypentyl)amino-6,7-dimethoxy-quinoline nitrate fumarate, m.p. 150°–152° C.
e. 2-(2,3-dihydroxypropyl)amino-quinoline.
f. 2-(2,3-dihydroxypropyl)amino-quinoline dinitrate maleate, m.p. 124° C. 124° C. (decomp.).
g. 2-(5-hydroxypentyl)amino-quinoline.
h. 2-(5-hydroxypentyl)amino-quinoline nitrate hydrochloride, m.p. 118.5°–120° C.
i. 2-[4-(2-hydroxyethyl)-1-piperazino]-6,7-dimethoxyquinoline, m.p. 176°–177° C.
j. 2-[4-(2-hydroxy)-1-piperazino]-6,7-dimethoxyquinoline nitrate dihydrochloride, m.p. 223°–226° C. (decomp.).

EXAMPLE 3

4-[3-Bis(2-hydroxyethyl)aminopropyl]amino-quinoline dinitrate dihydrochloride.

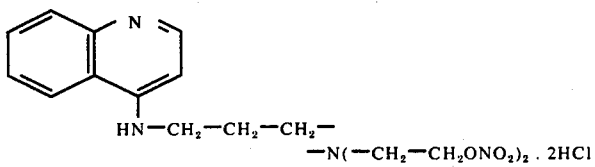

—N(—CH₂—CH₂ONO₂)₂ . 2HCl

Step A: Preparation of 4-[3-bis(2-hydroxyethyl)aminopropyl]amino-quinoline.

A mixture of 5.0 g. of 4-chloroquinoline, 7.2 g. of bis(2-hydroxyethyl)aminopropylamine, 3.0 g. of sodium carbonate and 25 ml. of isopropanol is heated in a pressure vessel at 150° C. for 17 hours. The resulting mixture is diluted with chloroform, filtered and purified by filtering over silica gel to obtain an oil of 4-[3-bis(2-hydroxyethyl)aminopropyl]amino-quinoline.

Step B: Preparation of 4-[3-bis(2-hydroxyethyl)aminopropyl]amino-quinoline dinitrate dihydrochloride A solution of 5.0 g. of 4-[3-bis(2-hydroxyethyl)aminopropyl]amino-quinoline in 5.0 g. of glacial acetic acid is added slowly to a mixture of 15 ml. of acetic anhydride and 5.0 ml. of 90% nitric acid with stirring at minus 5° C. The resulting mixture is allowed to warm to plus 5° C. and after standing for an additional 5 minutes it is treated with an excess of ice-cold aqueous ammonia solution and then extracted with methylene chloride to obtain an amber oil which is dissolved in 5.0 ml. of ethanol and treated with a slight excess of hydrogen chloride in ethanol. Addition of diethyl ether yields a solid which is recrystallized from methanol/diethyl ether to obtain 4-[3-bis(2-hydroxyethyl)aminopropyl]amino-quinoline dinitrate dihydrochloride, m.p. 125° C. (decomp.).

EXAMPLE 4

Following the procedure of Example 3 the following compounds are prepared:

a. 4-(4-(2-hydroxyethyl)-1-piperazino]-quinoline.
b. 4-[4-(2-hydroxyethyl)-1-piperazino]-quinoline nitrate dihydronitrate, m.p. 145° C. (decomp.).
c. 4-(5-hydroxypentyl)amino-6,7-dimethoxy-quinoline maleate, m.p. 146°–147° C.
d. 4-(5-hydroxypentyl)amino-6,7dimethoxy-quinoline nitrate hydrochloride.
e. 4-(2,3-dihydroxypropyl)amino-quinoline.
f. 4-(2,3-dihydroxypropyl)amino-quinoline dinitrate hydrochloride, m.p. 163° C.
g. 4-[4-(2-hydroxyethyl)-1-piperazino]-6,7-dimethoxy-quinoline.
h. 4-[4-(2-hydroxyethyl-1-piperazino]-6,7-dimethoxyquinoline nitrate dimaleate, m.p. 134°–135° C. (decomp.).
i. 4-[3-bis(2-hydroxyethyl)aminopropyl]amino-6,7-dimethoxy-quinoline.
j. 4-[3-bis(2-hydroxyethyl)aminopropyl]-6,7-dimethoxyquinoline dinitrate (as an oil), N.M.R. OCH₃ singlet δ 4.00,4.05 p.p.m., —CH₂—ONO₂ triplet δ 4.55 p.p.m., —NH broad singlet δ 4.62 p.p.m.
k. 2-(5-hydroxypentyl)amino-6-methoxy-quinoline, m.p. 111°–113.5° C.
l. 2-(5-hydroxypentyl)amino-6-methoxy-quinoline nitrate, maleate form, m.p. 123.5° – 124.5° C.
m. 2-[4(2-hydroxyethyl)-1-piperazino]-6-methoxy-quinoline, m.p. 126°–127° C.
n. 2-[4-(2-hydroxyethyl)-1-piperazino]-6-methoxy-quinoline nitrate, maleate form, m.p. 131°–132° C. (decomp.).
o. 2-[3-bis(hydroxyethyl)aminopropyl]amino-6-methoxy-quinoline, m.p. 97°–98.5° C.

p. 2-[3-bis(2-hydroxyethyl)aminopropyl]amino-6-methoxy-quinoline dinitrate, dihydronitrate form, m.p. 124°–125° C. (decomp.).

q. 4-(5-hydroxypentyl)amino-8-methoxy-quinoline, m.p. 138°–140° C.

r. 4-(5-hydroxypentyl)amino-8-methpoxy-quinoline nitrate, hydronitrate form, m.p. 149° C. (decomp.).

s. 4-[3-bis(2-hydroxyethyl)aminopropyl]amino-8-methoxy-quinoline, m.p. 141°–143° C.

t. 4-[3-bis(2-hydroxyethyl)aminopropyl]amino-8-methoxy-quinoline dinitrate difumarate form, m.p. 109°–110° C. (decomp.).

u. 2-[3-bis(2-hydroxyethyl)aminopropyl]amino-6,7-dimethoxy-quinoline, m.p. 88°–90° C.

v. 2-[3-bis(2-hydroxyethyl)aminopropyl]amino-6,7-dimethoxy-quinoline dinitrate fumarate form, m.p. 128°–130° C. (decomp.).

w. 2-[4-(2-hydroxyethyl)-1-piperazino]-6,7-dimethoxy-quinoline, m.p. 176°–177° C.

x. 2-[4-(2-hydroxyethyl)-1-piperazino]-6,7-dimethoxy-quinoline nitrate dihydrochloride, m.p. 223°–226° C.(decomp.).

y. 3-[3-bis(2-hydroxyethyl)aminopropyl]amino-quinoline.

z. 3-[3-bis(2-hydroxyethyl)aminopropyl]amino-quinoline dinitrate, as an oil, N.M.R. —CH$_2$ONO$_2$ triplet δ 4.62 p.p.m., —NH broad singlet δ 8.0 p.p.m., I.R. —ONO$_2$ strong peaks 1280 cm$^{-1}$, 1640 cm$^{-1}$, z-1. 4-[3-bis(2-hydroxyethyl)aminopropyl]amino-7-chloro-quinoline, m.p. 105.5°–107.5° C.

z-2. 4-[3-bis(2-hydroxyethyl)aminopropyl]amino-7-chloro-dinitrate trihydrochloride form, 140°–142° C.(decomp.).

z-3. 4-[4-(2-hydroxyethyl)-1-piperazino]-7-chloro-quinoline, m.p. 119°–121° C.

z-4. 4-[4-2-hydroxyethyl)-piperazino]-7-chloro-quinoline nitrate, dihydrochloride form, m.p. 150°–151° C.(decomp.).

z-5. 4-[3-bis(2-hydroxyethyl)aminopropyl]amino-6-methoxy-quinoline, dimaleate form, m.p. 144.5°–146° C.

z-6. 4-[3-bis(2-hydroxyethyl)aminopropyl]amino-6-methoxy-quinoline dinitrate, m.p. 80°–81° C.

z-7. 4-(5-hydroxypentyl)amino-7-methoxy-quinoline, m.p. 139°–140° C.

z-8. 4-(5-hydroxypentyl)amino-7-methoxy-quinoline nitrate, maleate form, m.p. 144.5°–146° C.

z-9. 4-[3-bis(2-hydroxyethyl)aminopropyl]amino-7-methoxyquinoline, m.p. 103.5°–106°° C.

z-10. 4-[3-bis(2-hydroxyethyl)aminopropyl]amino-7-methoxy-quinoline dinitrate difumarate form, m.p. 88° C.

z-11. 4-(5-hydroxypentyl)amino-6-methoxy-quinoline.

z-12. 4-(5-hydroxypentyl)amino-6-methoxy-quinoline nitrate maleate, m.p. 88°–90° C.

z-13. 4-(5-hydroxypentyl)amino-7-chloro-quinoline.

z-14. 4-(5-hydroxypentyl)amino-7-chloro-quinoline nitrate, hydrochloride form, m.p. 126°–128° C.

z-15. 4-(2,3-dihydroxypropyl)amino-7-chloro quinoline.

z-16. 4-(2,3-dihydroxypropyl)amino-7-chloro quinoline dinitrate, maleate form, m.p. 137°–138° C. (decomp.).

z-17. 4-{N-methyl-N-[3-bis(2-hydroxyethyl)aminopropyl]amino}-6,7-dimethoxy-quinoline difumarate form, m.p. 94°–95.5° C.

z-18. 4{N-methyl-N-[3-bis(2-hydroxyethyl)aminopropyl]amino}-6,7-dimethoxy-quinoline dinitrate difumarate form, as an oil, N.M.R. N—CH$_3$ singlet ~δ 3.1 p.p.m. —OCH$_3$ singlet~δ 3.9 p.p.m., —CH$_2$ONO$_2$ triplet~δ 4.5 p.p.m.

z-19 4-{N-methyl-N-[3-bis(2-hydroxyethyl)aminopropyl]amino}quinoline.

z-20. 4-{N-methyl-N-]3-bis(2-hydroxyethyl)aminopropyl]amino}quinoline difumarate form, m.p. 109°–110° C.

z-21. 4-(4-hydroxybutyl)amino-7-chloro-quinoline, m.p. 180° C.

z-22. 4-(4-hydroxybutyl)amino-7-chloro-quinoline nitrate, m.p. 142° C.

z-23. 4-(4-hydroxybutyl)amino-7-methoxy-quinoline, m.p. 128°–129° C.

z-24. 4-(4-hydroxybutyl)amino-7-methoxy-quinoline nitrate, m.p. 131° C.

z-25. 4-(4-hydroxybutyl)amino-8-methoxy-quinoline, m.p. 148°–150° C.

z-26. 4-(4-hydroxybutyl)amino-8-methoxy-quinoline nitrate hydrate hydrochloride.

z-27. 4-(6-hydroxyhexyl)amino-7-methoxy-quinoline, m.p. 124.5°–125.5° C.

z-28. 4-(6-hydroxyhexyl)amino-7-methoxy-quinoline nitrate hydrochloride, m.p. 145.5°–150° C. (decomp.).

z-29. 4-(6-hydroxyhexyl)amino-7-chloro-quinoline hydrochloride, m.p. 156°–157° C.

z-30. 4-(6-hydroxyhexyl)amino-7-chloro-quinoline nitrate hydrochloride, m.p. 145° C.

z-31. 4-[4-(2-hydroxyethyl)-1-piperazino]-6-methoxy-quinoline dihydrochloride, m.p. 255°–258° C.

z-32. 4-[4-(2-hydroxyethyl)-1-piperazino]-6-methoxy-quinoline nitrate dihydrochloride, m.p. 160° C.

z-33. 4-[4-(2-hydroxyethyl)-1-piperazino]-7-methoxy-quinoline, m.p. 122.5°—123.5° C.

z-34. 4-[4-(2-hydroxyethyl)-1-piperazino]-7-methoxy-quinoline nitrate, dihydronitrate form, m.p. 153° C.

z-35. 4-[4-(2-hydroxyethyl)-1-piperazino]-8-methoxy-quinoline, m.p. 162°–163° C.

z-36. 4-[4-(2-hydroxyethyl)-1-piperazino]-8-methoxy-quinoline nitrate dihydrochloride, m.p. 180° C. (decomp.).

z-37. 4-(6-hydroxyhexyl)amino-8-methoxy-quinoline.

z-38. 4-(6-hydroxyethyl)amino-8-methoxy-quinoline nitrate hydronitrate, m.p. 144°–147° C.

z-39. 4-(7-hydroxyheptyl)amino-7-chloroquinoline.

z-40. 4-(7-hydroxyheptyl)amino-7-chloroquinoline nitrate hydrochloride, m.p. 119.5°–121° C.

z-41. 4-(7-hydroxyheptyl)amino-7-methoxyquinoline.

z-42. 4-(7-hydroxyheptyl)amino-7-methoxyquinoline nitrate hydrochloride, m.p. 148°–148.5° C.

z-43. 4-(7-hydroxyheptyl)amino-8-methoxyquinoline.

z-44. 4-(7-hydroxyheptyl)amino-9-methoxyquinoline nitrate, hydronitrate form, m.p. 170°–173° C. (decomp.).

z-45. 4-(1,3-dihydroxypropyl)amino-6,7-dimethoxyquinoline.

z-46. 4-(1,3-dihydroxypropyl)amino-6,7-dimethoxyquinoline dinitrate hydrochloride.

EXAMPLE 5

1-Methyl-4-(5-hydroxypentyl)amino-7-chloro-quinoline nitrate iodide.

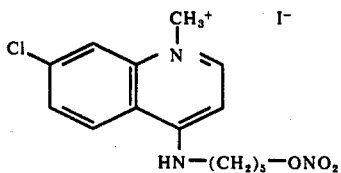

A mixture of 3.0 g. of 4-(5-hydroxypentyl)amino-7-chloro-quinoline nitrate and 20 ml. of methyl iodide is refluxed for 20 minutes. To the cooled reaction mixture is added dry diethyl ether to complete crystallization and the solids are collected by filtration, washed twice with diethyl ether and dried in a high vacuum to obtain 1-methyl-4-(5-hydroxypentyl)amino-7-chloro-quinoline nitrate iodide, m.p. 184°–186° C.(decomp).

EXAMPLE 6

Following the procedure of Example 5 the following additional compounds of the invention are prepared:
  a. 1-methyl-4-(5-hydroxypentyl)amino-7-chloro-quinoline iodide, 209°–211° C. (decomp.).
  b. 1-methyl-4-(5-hydroxypentyl)amino-6-methoxyquinoline nitrate iodide, m.p. 132°–133° C.
  c. 1-methyl-4-(5-hydroxypentyl)amino-7-methoxyquinoline nitrate iodide, m.p. 182°–183° C. (decomp.).
  d. 1-methyl-4-(5-hydroxypentyl)amino-6-methoxyquinoline iodide, m.p. 210°–212° C. (decomp.).
  e. 1-methyl-4-(5-hydroxypentyl)amino-8-methoxyquinoline nitrate iodide, m.p. 49°–51° C.
  f. 1-methyl-4-(5-hydroxypentyl)amino-8-methoxyquinoline iodide, m.p. 121°–122.5° C.
  g. 1-methyl-4-(4-hydroxybutyl)amino-7-chloroquinoline iodide, m.p. 231° C.
  h. 1-methyl-4-(4-hydroxybutyl)amino-7-chloroquinoline nitrate iodide, m.p. 160° C.
  i. 1-methyl-4-(4-hydroxybutyl)amino-7-methoxyquinoline iodide.
  j. 1-methyl-4-(4-hydroxybutyl)amino-7-methoxyquinoline nitrate iodide, m.p. 166° C.
  k. 1-methyl-4-(4-hydroxybutyl)amino-8-methoxyquinoline iodide, m.p. 127°–128.5° C.
  l. 1-methyl-4-(4-hydroxybutyl)amino-8-methoxyquinoline nitrate iodide, m.p. 126°–128° C.
  m. 1-methyl-4-(6-hydroxyhexyl)amino-7-chloroquinoline iodide, m.p. 223°–224° C.
  n. 1-methyl-4-(6-hydroxyhexyl)amino-7-chloroquinoline nitrate iodide, m.p. 170° C.
  o. 1-methyl-4-(6-hydroxyhexyl)amino-7-methoxyquinoline iodide, m.p. 209°–212° C.
  p. 1-methyl-4-(6-hydroxyhexyl)amino-7-methoxyquinoline nitrate iodide, m.p. 162°–164° C. (decomp.).
  q. 1-methyl-4-(6-hydroxyhexyl)amino-8-methoxyquinoline iodide, m.p. 88°–91° C.
  r. 1-methyl-4-(6-hydroxyhexyl)amino-8-methoxyquinoline nitrate iodide, m.p. 99°–100.5° C.
  s. 1-methyl-4-(7-hydroxyheptyl)amino-7-chloroquinoline nitrate iodide, m.p. 135° C.
  t. 1-methyl-4-(7-hydroxyheptyl)amino-7-methoxyquinoline nitrate iodide, m.p. 165° C. (decomp.).
  u. 1-methyl-4-(7-hydroxyheptyl)amino-8-methoxyquinoline nitrate iodide, m.p. 83°–86° C.
  v. 1-trifluoromethyl-4-(5-hydroxypentyl)amino-8-methoxyquinoline nitrate iodide.

What is claimed is:

1. A compound of the formula:

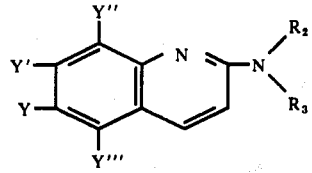

wherein
  $R_2$ is from the group of:
  a. $-CH_2(-CH_2)_n-OH$
  b. $-CH_2(-\overset{R_a^o}{\underset{|}{CH}})_n-OH$,
  c. $-\overset{R_a'}{\underset{|}{CH}}(-CH_2)_n-OH$, and
  d. $-CH_2(-CH_2)_x-N[CH_2(-CH_2)_y-OH]_2$ $R_3$ is from the group of:
  e. $-CH_2(-CH_2)_n-OH$ when $R_2$ is a) as above defined,
  f. hydrogen,
  g. lower alkyl of 1 to 4 carbon atoms,
  $R_a'$ is $-(CH_2-)_xCH_3$ or $-(CH_2-)_yOH$,
  $R_a^o$ is hydrogen, $-(CH_2-)_mCH_3$ or $-(CH_2-)_yOH$, provided that one $R_a^o$ is other than hydrogen, that the sum of n and m does not exceed 7 and that the sum of n and y does not exceed 8, or $R_2$ and $R_3$ together with the 4-amino nitrogen attached to quinoline ring form

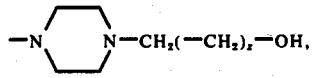

$n$ is 1 to 7,
$m$ is 0 to 4,
$x$ is 0 or 1,
$y$ is 1 to 4,
$z$ is 1 to 4, and
each of Y, Y', Y" and Y''' is hydrogen, halo of atomic weight of from 18 to 80, alkoxy of 1 to 3 carbon atoms, or alkyl of 1 to 3 carbon atoms, or Y and Y' together form methylenedioxy, provided at least 2 of Y, Y', Y" and Y''' are hydrogen and further provided that when one of Y, Y', Y", Y''' is halo then the others are hydrogen, or a pharmaceutically acceptable acid addition salt thereof.

2. A compound of claim 1 in which $R_3$ is hydrogen.
3. A compound of claim 2 in which $R_2$ is $-CH_2(-CH_2)_n-OH$.
4. A compound of claim 2 in which $R_2$ is $-CH_2(-CH_2)_x-N[-CH_2(-CH_2)_y-OH]_2$.
5. The compound of claim 4 in which Y', Y" and Y''' are hydrogen, Y is methoxy, z is 2 and y is 1.
6. The compound of claim 4 in which Y" and Y''' are hydrogen, Y and Y' are each methoxy, z is 2 and y is 1.

7. The compound of claim 1 in which $R_2$ is —$CH_2CHOHCH_2OH$, $R_3$ is hydrogen and each of Y, Y', Y" and Y''' is hydrogen.

8. A compound of claim 1 in which $R_2$ and $R_3$ together with the amino nitrogen attached to the quinoline ring form:

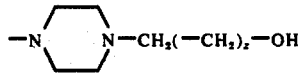

9. The compound of claim 8 in which z is 1, Y' is methoxy and Y, Y" and Y''' are each hydrogen.

10. The compound of claim 8 in which z is 1 and each of Y, Y', Y" and Y''' is hydrogen.

11. A compound of the formula:

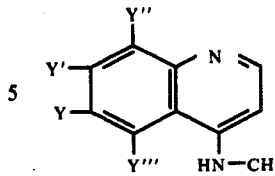

wherein
y is 1 to 4,
z is 1 to 4, and
each of Y, Y', Y" and Y''' is hydrogen, halo of atomic weight of from 18 to 80, alkoxy of 1 to 3 carbon atoms, or alkyl of 1 to 3 carbon atoms, or Y and Y' together form methylenedioxy, provided that at least 2 of Y, Y', Y" and Y''' are hydrogen and further provided that when one of Y, Y', Y" and Y''' is halo then the others are hydrogen, or a pharmaceutically acceptable acid addition salt thereof.

12. The compound of claim 11 in which Y, Y' and Y''' are hydrogen, Y" is methoxy, z is 2, y is 1.

* * * * *